United States Patent
Karathur et al.

(10) Patent No.: US 12,063,935 B2
(45) Date of Patent: Aug. 20, 2024

(54) METHODS FOR SEQUESTERING ATMOSPHERIC CARBON AND FOR QUANTIFYING THE SAME

(71) Applicant: Locus Solutions IPCo, LLC, Solon, OH (US)

(72) Inventors: Karthik N. Karathur, Solon, OH (US); Sean Farmer, Ft. Lauderdale, FL (US)

(73) Assignee: LOCUS SOLUTIONS IPCO, LLC, Solon, OH (US)

(*) Notice: Subject to any disclaimer, the term of this patent is extended or adjusted under 35 U.S.C. 154(b) by 208 days.

(21) Appl. No.: 17/514,391

(22) Filed: Oct. 29, 2021

(65) Prior Publication Data

US 2022/0132865 A1 May 5, 2022

Related U.S. Application Data

(60) Provisional application No. 63/110,070, filed on Nov. 5, 2020.

(51) Int. Cl.
| | |
|---|---|
| *A01N 63/38* | (2020.01) |
| *A01C 23/04* | (2006.01) |
| *A01N 63/22* | (2020.01) |
| *C05G 3/80* | (2020.01) |
| *C08L 101/00* | (2006.01) |
| *C12N 1/14* | (2006.01) |
| *C12N 1/20* | (2006.01) |
| *C12R 1/07* | (2006.01) |
| *C12R 1/885* | (2006.01) |

(52) U.S. Cl.
CPC ............ *A01N 63/38* (2020.01); *A01C 23/047* (2013.01); *A01N 63/22* (2020.01); *C08L 101/00* (2013.01); *C12N 1/14* (2013.01); *C12N 1/20* (2013.01); *C05G 3/80* (2020.02); *C12R 2001/07* (2021.05); *C12R 2001/885* (2021.05)

(58) Field of Classification Search
None
See application file for complete search history.

(56) References Cited

U.S. PATENT DOCUMENTS

| | | | | |
|---|---|---|---|---|
| 8,716,001 B2 * | 5/2014 | Harman | ................. | A01N 63/38 |
| | | | | 435/254.6 |
| 8,877,480 B2 * | 11/2014 | Harman | ................. | C12N 1/145 |
| | | | | 435/254.6 |
| 8,877,481 B2 * | 11/2014 | Harman | ................. | A01N 63/38 |
| | | | | 435/254.6 |
| 2020/0308611 A1 | 10/2020 | Senaratne et al. | | |

FOREIGN PATENT DOCUMENTS

| | | | |
|---|---|---|---|
| CN | 102964178 A | * | 3/2013 |
| WO | 2020076797 A1 | | 4/2020 |
| WO | 2020210074 A1 | | 10/2020 |

OTHER PUBLICATIONS

Bennett, A.E., et al. "Plant lignin content altered by soil microbial community." New Phytologist, 2015, 206: 166-174.
Graça, J. "Suberin: the biopolyester at the frontier of plants." Frontiers in Chemistry, Oct. 2015, 3(62): 1-11.
Salas-González, I., et al. "Coordination between microbiota and root endodermis supports plant mineral nutrient homeostasis." Science, 2021, 371(6525): eabd0695, pp. 1-11.
Singh, U.B., et al. "Trichoderma harzianum- and Methyl Jasmonate-Induced Resistance to Bipolaris sorokiniana Through Enhanced Phenylpropanoid Activities in Bread Wheat (*Triticum aestivum* L.)." Frontiers in Microbiology, Jul. 2019, 10(1697): 1-19.
Suseela, V., et al. "Warming and elevated CO2 alter the suberin chemistry in roots of photosynthetically divergent grass species." AoB Plants, 2017, 9(5): 1-11.

* cited by examiner

*Primary Examiner* — Alton N Pryor
(74) *Attorney, Agent, or Firm* — SALIWANCHIK, LLOYD & EISENSCHENK

(57) ABSTRACT

The subject invention provides materials and methods for reducing deleterious atmospheric gases, such as greenhouse gases (GHGs) by enhancing utilization and storage of carbon in plants, as well as increasing the sequestration of carbon in plant and soil matter in the form of degradation-resistant organic polymers.

18 Claims, No Drawings

METHODS FOR SEQUESTERING ATMOSPHERIC CARBON AND FOR QUANTIFYING THE SAME

CROSS-REFERENCE TO RELATED APPLICATION

This application claims the benefit of U.S. provisional patent application No. 63/110,070 filed Nov. 5, 2020, which is incorporated by reference herein in its entirety.

BACKGROUND OF THE INVENTION

Gases that trap heat in the atmosphere are called "greenhouse gases," or "GHG," and include carbon dioxide, methane, nitrous oxide and fluorinated gases (Climate Change Indicators in the United States, 2016, fourth edition, United States Environmental Protection Agency at 6, hereinafter "EPA report 2016").

Carbon dioxide ($CO_2$) enters the atmosphere through burning fossil fuels (coal, natural gas, and oil), solid waste, trees and wood products, and also as a result of certain chemical reactions, e.g., the manufacture of cement. Carbon dioxide is removed from the atmosphere by, for example, absorption by plants as part of the biological carbon cycle.

Methane ($CH_4$) is emitted during the production and transport of coal, natural gas, and oil. Methane emissions also result from production of livestock animals, many of whose digestive systems comprise methanogenic microorganisms. Furthermore, other agricultural practices, and the decay of organic waste in lagoons and municipal solid waste landfills can produce methane emissions.

Nitrous oxide ($N_2O$) is emitted during industrial activities and during combustion of fossil fuels and solid waste. In agriculture, over-application of nitrogen-containing fertilizers and poor soil management practices can also lead to increased nitrous oxide emissions.

Fluorinated gases including, e.g., hydrofluorocarbons, perfluorocarbons, sulfur hexafluoride, and nitrogen trifluoride are synthetic, powerful greenhouse gases that are emitted from a variety of industrial processes (Overview of Greenhouse Gases 2016).

Based on recent measurements from monitoring stations around the world and measurement of older air from air bubbles trapped in layers of ice from Antarctica and Greenland, global atmospheric concentrations of, e.g., carbon dioxide, have risen significantly over the last few hundred years (EPA report 2016 at, e.g., 6, 15).

Especially since the Industrial Revolution began in the 1700s, human activity has contributed to the amount of greenhouse gases in the atmosphere by burning fossil fuels, cutting down forests, and conducting other industrial activities. Many greenhouse gases emitted into the atmosphere remain there for long periods of time ranging from a decade to many millennia. Over time these gases are removed from the atmosphere by chemical reactions or by emissions sinks, such as the oceans and vegetation that absorb greenhouse gases from the atmosphere.

Because each greenhouse gas has a different lifetime and a different ability to trap heat in the atmosphere and in order to be able to compare different gases, emissions are generally converted into carbon dioxide equivalents using each gas's global warming potential, which measures how much a given amount of the gas is estimated to contribute to global warming over a period of 100 years after being emitted.

Based on these considerations, the EPA determined that the heating effect caused by greenhouse gases, also termed "radiative forcing," has increased by about 37% since 1990 (EPA report 2016 at 16).

Although global emissions of all major greenhouse gases increased between 1990 and 2010, the net emissions of carbon dioxide, which accounts for about three-fourths of the total global emissions, increased by 42%, whereas emissions of methane increased by about 15%, emissions of fluorinated gases doubled, and emission of nitrous oxide emissions increased by about 9% (EPA report 2016 at 14).

World leaders have attempted to curb the increase of GHG emissions through treaties and other inter-state agreements. One such attempt is through the use of carbon credit systems. A carbon credit is a generic term for a tradable certificate or permit representing the right to emit one ton of carbon dioxide, or an equivalent GHG. In a typical carbon credit system, a governing body sets quotas on the amount of GHG emissions an operator can produce. Exceeding these quotas requires the operator to purchase extra allowances from other operators who have not used all of their carbon credits.

One goal of carbon credit systems is to encourage companies to invest in more green technology, machinery and practices in order to benefit from the trade of these credits. Under the Kyoto Protocol of the United Nations Framework Convention On Climate Change (UNFCCC), a large number of countries have agreed to be bound internationally by policies for GHG reduction, including through trade of emissions credits. While the United States is not bound by the Kyoto Protocol, and while there is no central national emissions trading system in the U.S., some states, such as California and a group of northeastern states, have begun to adopt such trading schemes.

One strategy for reducing atmospheric $CO_2$ levels is carbon sequestration, or transfer of carbon from, e.g., the atmosphere to soil organic matter. Carbon is exchanged among the biosphere, pedosphere, hydrosphere, lithosphere, and atmosphere of the Earth and is stored in the following major sinks: (1) as organic molecules in living and dead organisms of the biosphere; (2) as $CO_2$ in the atmosphere; (3) as organic matter in soils; (4) as fossil fuels and sedimentary rocks such as limestone, dolomite, and chalk in the lithosphere; and (5) in the oceans as dissolved $CO_2$ and calcium carbonate shells of marine organisms (see, e.g., Pidwirny 2006).

Dependent on the nature of the carbon sink, carbon sequestration can be achieved in several ways: by inorganic chemical reactions that cause $CO_2$ in the form of carbonates/bicarbonates to bond with dissolved minerals and salts to form compounds such as calcium and magnesium carbonates; by plant photosynthesis, which uses sunlight to combine $CO_2$ from the air and water to from glucose that is stored in the tissue of plants; by plant biomass growth, where the amount of above- and below-ground plant tissue comprising carbon-rich molecules is increased; and indirectly by microbial decomposition of the biomass of plant and animal tissue into other compounds such as, e.g., carbohydrates, proteins, organic acids, humic substances, waxes, coal, oil, and natural gas.

Global warming may contribute to steeper temperature fluctuations, increased global precipitation, flooding and droughts, and changes in sea surface temperature and sea levels; thus, there exists a need to reduce greenhouse gases, especially $CO_2$, to slow these detrimental effects.

BRIEF SUMMARY OF THE INVENTION

The subject invention provides materials and methods for reducing deleterious atmospheric gases, such as greenhouse gases (GHGs). In specific embodiments, the reduction in deleterious atmospheric gases is achieved by enhancing utilization and storage of carbon in plants, as well as increasing the sequestration of carbon in plant and soil matter.

In preferred embodiments, the subject invention provides methods for reducing atmospheric carbon dioxide, wherein a composition comprising one or more beneficial soil-colonizing microorganisms and/or growth by-products thereof is applied to a part of a plant (e.g., the roots) and/or its surrounding environment (e.g., soil).

In certain embodiments, the one or more microorganisms colonize the soil and/or roots of the plants, and provide one or more benefits to the plants that result in enhanced utilization and storage of carbon via enhanced growth and/or health of both aerial and subterranean plant tissue.

In certain embodiments, the plant tissue comprises degradation-resistant organic polymers. Thus, in preferred embodiments, the methods of the subject invention result in increased accumulation of these degradation-resistant organic polymers in plant tissues.

In certain embodiments, the degradation-resistant organic polymers are polysaccharides, polyaromatics and/or polyesters. In preferred embodiments, the degradation-resistant organic polymers are not readily biodegradable, e.g., for at least 10, 15, or 25 years or more. Examples of degradation-resistant organic polymers found in plants include, but are not limited to, suberin, cutin, cutan and lignin.

In specific embodiments, the degradation-resistant organic polymer is suberin, a polyester found mostly in the cell walls of the external layers of plant tissue, where it serves as a protective barrier between the interior plant tissues and the external environment.

In addition to enhancing plant utilization and storage of carbon, application of the composition can also increase soil carbon sequestration. In certain embodiments, increasing soil carbon sequestration is achieved by enhancing the growth of plant roots in the soil and/or increasing accumulation of degradation-resistant organic polymers in the plant roots.

In certain embodiments, the plants treated according to the subject invention are living perennial plants. Enhanced growth and/or health of the perennial plant can also result in enhanced accumulation, and thus sequestration, of carbon in the form of, for example, degradation-resistant organic polymers present in both aerial and subterranean plant tissue. Advantageously, carbon sequestered in this form can remain sequestered for an indefinite time period and/or for as long as the plant is alive. Even further, as the plant grows in size and accumulates additional degradation-resistant organic polymers, the amount of carbon that is sequestered will continue to increase through the life of the plant.

In certain embodiments, the plants are annuals and/or crops plants, wherein portions of plant tissue are left behind after the plant's death and/or after harvesting of the aerial tissue.

In preferred embodiments, the remaining plant tissue is covered by soil. In some embodiments, the remaining plant tissue is subterranean tissue (e.g., root tissue) that is already located beneath ground level. In some embodiments, the remaining plant tissue is aerial tissue (e.g., stalks and/or leaves), which is preferably buried at a depth below the soil that is undisturbed by tilling.

Advantageously, in certain embodiments, the degradation-resistant organic polymer(s) in the remaining plant tissue do not decompose for many years, e.g., at least 5, 10, 25 50, or 100 years, or more after the death of the plant. Thus, while other portions of the plant tissue may decompose, the degradation-resistant organic polymer(s) remain in the soil to sequester carbon therein without being disturbed by tilling or movement of the top layers of soil.

In preferred embodiments, the subject methods also comprise performing one or more measurements to assess the effect of the methods of the subject invention on the generation and/or reduction in generation of GHGs, and/or the accumulation of carbon in plants and/or soil.

In certain embodiments, assessing GHG generation can take the form of measuring GHG emissions before and after employing the subject methods. Measuring GHG emissions can comprise direct emissions measurement and/or analysis of fuel input.

In certain embodiments, carbon content of a site, e.g., an agricultural site, a turf or sod farm, a pasture, or a forest ecosystem, can be measured by, for example, quantifying the aboveground and/or below-ground biomass of plants. In some embodiments, the carbon concentration of, for example, a tree, is assumed to be from about 40 to 50% of the biomass.

Biomass quantification can take the form of, for example, harvesting plants in a sample area and measuring the weight of the different parts of the plant before and after drying. Biomass quantification can also be carried out using non-destructive, observational methods, such as measuring, e.g., trunk diameter, height, volume, and other physical parameters of the plant. Remote quantification can also be used, such as, for example, laser profiling and analysis by drones.

In some embodiments, carbon content of an agricultural site, a sod or turf farm, a pasture or prairie, an aquatic ecosystem or a forest ecosystem, can further comprise sampling and measuring carbon content of litter, woody debris and/or soil organic matter of a sampling area.

In one embodiment, the assessment comprises quantifying the amount of suberin and/or other degradation-resistant organic polymers accumulated in a sample of plant tissue and/or soil treated according to the subject methods. Such assessments can comprise, for example, histological analysis and/or chromatographic studies.

In some embodiments, the subject invention can be used for reducing the number of carbon credits used by an operator involved in, e.g., agriculture, livestock production, forestry/reforestation, and pasture management. In some embodiments, the subject invention can be used for "carbon farming," where plants are grown for the purpose of sequestering carbon in tracts of land.

In certain embodiments, the subject invention provides microbe-based products, as well as methods of using these microbe-based products for reduction of atmospheric GHGs, increased utilization of carbon and/or enhanced sequestration of carbon. In one embodiment, the subject invention provides microbe-based compositions that can enhance the properties of soil, and enhance the above- and below-ground biomass of plants—including degradation-resistant organic polymers such as suberin. Advantageously, the microbe-based products and methods of the subject invention are environmentally-friendly, non-toxic and cost-effective.

DETAILED DESCRIPTION OF THE INVENTION

The subject invention provides materials and methods for reducing deleterious atmospheric gases, such as greenhouse gases (GHGs). In specific embodiments, the reduction in deleterious atmospheric gases is achieved by enhancing utilization and storage of carbon in plants, as well as increasing the sequestration of carbon in soil matter via accumulation of degradation-resistant organic polymers in subterranean plant tissue and/or soil.

In certain embodiments, methods for assessing and/or quantifying carbon sequestration in plant matter and/or soil matter are also provided.

Selected Definitions

As used herein, "agriculture" means the cultivation and breeding of plants for food, fiber, biofuel, medicines, cosmetics, supplements, ornamental purposes and other uses. According to the subject invention, agriculture can also include horticulture, landscaping, gardening, plant conservation, forestry and reforestation, pasture and prairie restoration, orcharding, arboriculture, and agronomy. Further included in agriculture are the care, monitoring and maintenance of soil.

As used herein, the term "control" used in reference to a pest means killing, disabling, immobilizing, or reducing population numbers of a pest, or otherwise rendering the pest substantially incapable of causing harm.

As used herein, an "isolated" or "purified" compound is substantially free of other compounds, such as cellular material, with which it is associated in nature. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. "Isolated" in the context of a microbial strain means that the strain is removed from the environment in which it exists in nature. Thus, the isolated strain may exist as, for example, a biologically pure culture, or as spores (or other forms of the strain) in association with a carrier.

As used herein, a "biologically pure culture" is a culture that has been isolated from materials with which it is associated in nature. In a preferred embodiment, the culture has been isolated from all other living cells. In further preferred embodiments, the biologically pure culture has advantageous characteristics compared to a culture of the same microbe as it exists in nature. The advantageous characteristics can be, for example, enhanced production of one or more growth by-products.

In certain embodiments, purified compounds are at least 60% by weight the compound of interest. Preferably, the preparation is at least 75%, more preferably at least 90%, and most preferably at least 99%, by weight the compound of interest. For example, a purified compound is one that is at least 85%, 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

As used herein, "enhancing" means improving or increasing. For example, enhanced plant health means improving the plant's ability grow and thrive, which includes increased seed germination and/or emergence, improved ability to ward off pests and/or diseases, and improved ability to survive environmental stressors, such as droughts and/or overwatering. Enhanced plant growth and/or enhanced plant biomass means increasing the size and/or mass of a plant both above and below the ground (e.g., increased canopy/foliar volume, height, trunk caliper, branch length, shoot length, protein content, root size/density and/or overall growth index), and/or improving the ability of the plant to reach a desired size and/or mass. Enhanced yields mean improving the end products produced by the plants in a crop, for example, by increasing the number and/or size of fruits, leaves, roots and/or tubers per plant, and/or improving the quality of the fruits, leaves, roots and/or tubers (e.g., improving taste, texture, brix, chlorophyll content and/or color).

A "metabolite" refers to any substance produced by metabolism (e.g., a growth by-product) or a substance necessary for taking part in a particular metabolic process. A metabolite can be an organic compound that is a starting material, an intermediate in, or an end product of metabolism. Examples of metabolites include, but are not limited to, biosurfactants, biopolymers, enzymes, acids, solvents, alcohols, proteins, vitamins, minerals, microelements, and amino acids.

The subject invention utilizes "microbe-based compositions," meaning a composition that comprises components that were produced as the result of the growth of microorganisms or other cell cultures. Thus, the microbe-based composition may comprise the microbes themselves and/or by-products of microbial growth. The microbes may be in a vegetative state, in spore or conidia form, in hyphae form, in any other form of propagule, or a mixture of these. The microbes may be planktonic or in a biofilm form, or a mixture of both. The by-products of growth may be, for example, metabolites, cell membrane components, proteins, and/or other cellular components. The microbes may be intact or lysed. In preferred embodiments, the microbes are present, with growth medium in which they were grown, in the microbe-based composition. The microbes may be present at, for example, a concentration of at least $1\times10^4$, $1\times10^5$, $1\times10^6$, $1\times10^7$, $1\times10^8$, $1\times10^9$, $1\times10^{10}$, $1\times10^{11}$, $1\times10^{12}$ or $1\times10^{13}$ or more CFU per gram or per ml of the composition.

The subject invention further provides "microbe-based products," which are products that are to be applied in practice to achieve a desired result. The microbe-based product can be simply a microbe-based composition harvested from a microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, "polymer" refers to any macromolecular compound prepared by bonding one or more similar molecular units, called monomers, together. Polymers include synthetic and natural polymers. Exemplary polymers include rubbers, starches, resins, gums (e.g., guar gum, xanthan gum, and welan gum), neoprene, nylon, PVC, silicone, cellulose, polystyrene, polyethylene, polypropylene, polyacrylonitrile, polyamines, polysaccharides (e.g., levan), polynucleotides, polybutylene adipate terephthalate (PBAT), polyhydroxyalkanoates (PHAs), polybytlene succinate (PBS), polycaprolactone (PCL), polyglycolic acid (PGA), polyhydroxybutyrates (PHBs), polyesters such as polylactide (PLA), polyacrylamides (PAM), and others.

Further included in the term polymer is the term "biopolymer," "biological polymer" or "organic polymer," which as used herein, means a natural polymeric substance, or a polymeric substance occurring in, or produced by, a living organism. Biopolymers can include, for example, polynucleotides, polysaccharides, polyesters, and polypeptides. Specific examples of biopolymers include, but are not limited to, rubbers, suberin, melanin, lignin, cellulose, xanthan gum, guar gum, welan gum, levan, alginate, and many others.

As used herein, a "pest" is any organism, other than a human, that is destructive, deleterious and/or detrimental to humans or human concerns (e.g., agriculture, horticulture). In some, but not all instances, a pest may be a pathogenic organism. Pests may cause or be a vector for infections, infestations and/or disease, or they may simply feed on or cause other physical harm to living tissue. Pests may be single- or multi-cellular organisms, including but not limited to, viruses, fungi, bacteria, parasites, protozoa and/or nematodes.

As used herein "preventing" or "prevention" of a situation or occurrence means delaying, inhibiting, suppressing, forestalling, and/or minimizing the onset, extensiveness or progression of the situation or occurrence. Prevention can include, but does not require, indefinite, absolute or complete prevention, meaning it may still develop at a later time. Prevention can include reducing the severity of the onset of such a situation or occurrence, and/or stalling its development to a more severe or extensive situation or occurrence.

Ranges provided herein are understood to be shorthand for all of the values within the range. For example, a range of 1 to 20 is understood to include any number, combination of numbers, or sub-range from the group consisting of 1, 2, 3, 4, 5, 6, 7, 8, 9, 10, 11, 12, 13, 14, 15, 16, 17, 18, 19, 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated.

For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, "reduction" refers to a negative alteration, and the term "increase" refers to a positive alteration, wherein the negative or positive alteration is at least 0.25%, 0.5%, 1%, 5%, 10%, 15%, 20%, 25%, 30%, 35%, 40%, 45%, 50%, 55%, 60%, 70%, 75%, 80%, 85%, 90%, 95%, or 100%.

As used herein, "reference" refers to a standard or control condition.

As used herein, a "soil amendment" or a "soil conditioner" is any compound, material, or combination of compounds or materials that are added into soil to enhance the properties of the soil and/or rhizosphere. Soil amendments can include organic and inorganic matter, and can further include, for example, fertilizers, pesticides and/or herbicides. Nutrient-rich, well-draining soil is essential for the growth and health of plants, and thus, soil amendments can be used for enhancing the plant biomass by altering the nutrient and moisture content of soil. Soil amendments can also be used for improving many different qualities of soil, including but not limited to, soil structure (e.g., preventing compaction); improving the nutrient concentration and storage capabilities; improving water retention in dry soils; and improving drainage in waterlogged soils.

As used herein, "surfactant" refers to a compound that lowers the surface tension (or interfacial tension) between phases. Surfactants act as, e.g., detergents, wetting agents, emulsifiers, foaming agents, and dispersants. A "biosurfactant" is a surfactant produced by a living organism.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. Use of the term "comprising" contemplates other embodiments that "consist" or "consist essentially" of the recited component(s).

Unless specifically stated or obvious from context, as used herein, the term "or" is understood to be inclusive. Unless specifically stated or obvious from context, as used herein, the terms "a," "and" and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All references cited herein are hereby incorporated by reference in their entirety.

Sequestration and Quantification of Carbon

In preferred embodiments, the subject invention provides methods for reducing atmospheric carbon dioxide levels, wherein a composition comprising one or more beneficial soil-colonizing microorganisms and/or growth by-products thereof is applied to a part of a plant (e.g., the roots) and/or its surrounding environment (e.g., soil).

In certain embodiments, the one or more microorganisms colonize the soil and/or roots of the plants, and provide one or more benefits to the plants that result in enhanced utilization and storage of carbon via enhanced growth and/or health of both aerial and subterranean plant tissue.

In some embodiments, the subject methods increase the above- and below-ground biomass of plants, which includes, for example, increased foliage volume, increased stem and/or trunk diameter, enhanced root growth and/or density, and/or increased total numbers of plants. In one embodiment, this is achieved by improving the overall hospitability of the rhizosphere in which a plant's roots are growing, for example, by improving the nutrient and/or moisture retention properties of the rhizosphere.

In some embodiments, the microorganisms of the subject microbe-based compositions can promote colonization of the roots and/or rhizosphere by, for example, aerobic bacteria, yeasts, and/or fungi.

In one embodiment, the promotion of colonization can lead to improved biodiversity of the soil microbiome. As used herein, improving the biodiversity refers to increasing the variety of microbial species within the soil. In some embodiments, improved biodiversity comprises increasing the ratio of aerobic bacterial species, yeast species, and/or fungal species to anaerobic microorganisms in the soil.

For example, in one embodiment, the microbes of the subject composition can colonize roots, the soil and/or the rhizosphere and encourage colonization of other nutrient-fixing microbes, such as *Rhizobium* and/or *Mycorrhizae,* and other endogenous and/or exogenous microbes that promote accumulation of carbon-rich plant tissue.

In one embodiment, improved soil biodiversity promotes enhanced nutrient solubilization and/or uptake. For example, certain aerobic bacterial species, such as *Bacillus amyloliquefaciens*, can acidify the soil and solubilize NPK fertilizers into plant-usable forms.

In one embodiment, the method can be used for enhancing penetration of beneficial molecules through the outer layers of root cells, for example, at the root-soil interface of the rhizosphere.

In preferred embodiments, the subject method enhances plant utilization and storage of carbon, which is achieved by enhancing the accumulation of degradation-resistant organic polymers in plant tissue and/or soil. In some embodiments, the accumulation of degradation-resistant organic polymers is further enhanced by utilizing plants that have been modified to produce greater-than-normal amounts of a particular degradation-resistant organic polymer.

In certain embodiments, the degradation-resistant organic polymers are polysaccharides, polyaromatics and/or polyesters. Examples found in plants include, but are not limited to, suberin, cutin, cutan, and lignins. In preferred embodiments, due to, for example, the complex nature of their chemical structure, the degradation-resistant organic polymers are not readily biodegradable for, e.g., at least 1 year, at least 5 years, at least 25 years, at least 100 years, or even at least 1,000 years after the death of the plant.

In one embodiment, the degradation-resistant organic polymer is lignin. Lignin, as used herein, is the generic term for a group of aromatic cross-linked polymers present in the cell walls of support tissues of vascular plants and some algae. The main building blocks of lignin are the hydroxycinnamyl alcohols (or monolignols) coniferyl alcohol and sinapyl alcohol, with minor amounts of p-coumaryl alcohol.

Lignins are important in the formation of cell walls in wood and bark, as they do not decompose readily and provide rigid structure to plants. Additionally, lignins protect cell wall polysaccharides from microbial degradation, making them resistant to decay. Biosynthesis of lignins can be induced in plants by stressors such as wounding, infection, metabolic stress and alterations of cell wall structure.

In one embodiment, the degradation-resistant organic polymer is cutin and/or cutan, both of which are waxy polymers that form the hydrophobic plant cuticle. The cuticle covers all aerial surfaces of plants and helps prevent water loss and/or over-heating. Cutin is a polyester comprising inter-esterified omega hydroxyl acids, which are cross-linked by ester and epoxide bonds. Cutan is a non-saponifiable hydrocarbon polymer that is substantially resistant to decay.

In one specific embodiment, the degradation-resistant organic polymer is suberin, a lipophilic macromolecule found in specialized plant cell walls, wherever insulation or protection toward the surroundings is needed. More specifically, suberin is a polyester comprised of phenylpropanoids, long chain fatty acids and fatty alcohols, as well as hydroxyl fatty acids and dicarboxylic acids. Suberin is a cell wall constituent that acts as a highly efficient barrier limiting water, solute, gas and ion exchange. Suberized cell walls can also restrict pathogen invasion and provide a barrier to radial oxygen loss from roots to an anaerobic root substrate in some plants.

In addition to enhancing plant utilization and storage of carbon, colonization of the roots and/or soil by the microbes of the subject composition can also increase soil carbon sequestration. In certain embodiments, increasing soil carbon sequestration is achieved by enhancing the growth of plant roots in the soil and/or increasing accumulation of degradation-resistant organic polymers in the plant roots.

In certain embodiments, the plants treated according to the subject invention are living perennial plants. Enhanced growth and/or health of the perennial plant can also result in enhanced accumulation, and thus sequestration, of carbon in the form of degradation-resistant organic polymers present in both aerial and subterranean plant tissue. Advantageously, carbon sequestered in this form can remain sequestered for an indefinite time period and/or for as long as the plant is alive. Even further, as the plant grows in size and accumulates additional degradation-resistant organic polymers, the amount of carbon that is sequestered will continue to increase through the life of the plant.

In certain embodiments, the plants are annuals and/or crops plants, wherein portions of plant tissue are left behind after the plant's death and/or after harvesting of the aerial tissue.

In preferred embodiments, the remaining plant tissue is covered by soil. In some embodiments, the remaining plant tissue is subterranean tissue (e.g., root tissue) that is already located beneath ground level. In some embodiments, the remaining plant tissue is aerial tissue (e.g., stalks and/or leaves), which is preferably buried at a depth below the soil that is undisturbed by tiling.

Advantageously, in certain embodiments, the degradation-resistant organic polymers in the remaining plant tissue do not decompose for many years, e.g., at least 25 years, at least 100 years, or even at least 1,000 years after the death of the plant. Thus, while other portions of the plant tissue may decompose, the degradation-resistant organic polymers remain in the soil to sequester carbon therein without being disturbed by tilling or movement of the top layers of soil.

In some embodiments, the interaction between the microorganisms and the roots of a plant encourage the accumulation and/or increased accumulation of degradation-resistant organic polymers in the roots. In one embodiment, this is due to microscopic openings made in the roots by the microbes as they form associations with the roots, which stimulates the biosynthesis of protective barrier molecules, such as suberin and/or lignin.

In some embodiments, prior to applying a composition to the site, the method comprises assessing the site for local conditions, determining a preferred formulation for the composition (e.g., the type, combination and/or ratios of microorganisms and/or growth by-products) that is customized for the local conditions, and producing the composition with the preferred formulation.

The local conditions can include, for example, soil conditions (e.g., soil type, species of soil microbiota, amount and/or type of soil organic content, amount and/or type of GHG precursor substrates, amount and/or type of fertilizers or other soil additives or amendments present); crop and/or plant conditions (e.g., types, numbers, age and/or health of plants being grown); environmental conditions (e.g., current climate, season, or time of year); amount and type of GHG emissions at the site; mode and/or rate of application of the composition, and others as are relevant to the site.

After assessment, a preferred formulation for the composition can be determined so that the composition can be customized for these local conditions. The composition is then cultivated, preferably at a microbe growth facility that is within 300 miles of the site of application, preferably within 200 miles, even more preferably within 100 miles.

In some embodiments the local conditions are assessed periodically, for example, once annually, biannually, or even monthly. In this way, the composition formula can be modified in real time as necessary to meet the unique needs of the changing local conditions.

In preferred embodiments, the subject methods also comprise performing one or more measurements to assess the effect of the methods of the subject invention on the generation and/or reduction in generation of GHGs and/or on the accumulation of carbon in plants and/or soil.

Measurements can be conducted at a certain time point after application of the microbe-based composition to the site. In some embodiments, the measurements are conducted after about 1 week or less, 2 weeks or less, 3 weeks or less, 4 weeks or less, 30 days or less, 60 days or less, 90 days or less, 120 days or less, 180 days or less, and/or 1 year or less.

Furthermore, the measurements can be repeated over time. In some embodiments, the measurements are repeated daily, weekly, monthly, bi-monthly, semi-monthly, semi-annually, and/or annually.

In certain embodiments, assessing GHG generation can take the form of measuring GHG emissions from a site. Gas chromatography with electron capture detection is commonly used for testing samples in a lab setting. In certain embodiments, GHG emissions can also be conducted in the field, using, for example, flux measurements and/or in situ soil probing. Flux measurements analyze the emission of gases from the soil surface to the atmosphere, for example, using chambers that enclose an area of soil and then estimate flux by observing the accumulation of gases inside the chamber over a period of time. Probes can be used to generate a soil gas profile, starting with a measurement of the concentration of the gases of interest at a certain depth in the soil, and comparing it directly between probes and ambient surface conditions (Brummell and Siciliano 2011, at 118).

Measuring GHG emissions can also comprise other forms of direct emissions measurement, gas chromatography-mass spectrometry (GC-MS) and/or analysis of fuel input. Direct emissions measurements can comprise, for example, identifying polluting operational activities (e.g., fuel-burning automobiles) and measuring the emissions of those activities directly through Continuous Emissions Monitoring Systems (CEMS). Fuel input analysis can comprise calculating the quantity of energy resources used (e.g., amount of electricity, fuel, wood, biomass, etc., consumed) determining the content of, for example, carbon, in the fuel source, and applying that carbon content to the quantity of the fuel consumed to determine the amount of emissions.

In certain embodiments, carbon content of a site where plants are growing, e.g., agricultural site, crop, sod or turf farm, pasture/prairie or forest, can be measured by, for example, quantifying the aboveground and/or below-ground biomass of plants. In general, the carbon concentration of, for example, a tree, is assumed to be from about 40 to 50% of the biomass.

Biomass quantification can take the form of, for example, harvesting plants in a sample area and measuring the weight of the different parts of the plant before and after drying. Biomass quantification can also be carried out using non-destructive, observational methods, such as measuring, e.g., trunk diameter, height, volume, and other physical parameters of the plant. Remote quantification can also be used, such as, for example, laser profiling and/or drone analysis.

In some embodiments, carbon content of a site can further comprise sampling and measuring carbon content of litter, woody debris and/or soil of a sampling area. Soil, in particular, can be analyzed, for example, using dry combustion to determine percent total organic carbon (TOC); by potassium permanganate oxidation analysis for detecting active carbon; and by bulk density measurements (weight per unit volume) for converting from percent carbon to tons/acre.

In one embodiment, the assessment comprises identifying the type, and/or quantifying the amount, of a degradation-resistant organic polymer accumulated in a sample of plant tissue and/or soil treated according to the subject methods. Preferably, the method is ubiquitously applicable and/or adaptable to assessing all plant types.

In one embodiment, the assessment comprises conducting a histological analysis of plant tissue. In one embodiment, the assessment comprises extracting and, optionally, solubilizing the degradation-resistant organic polymer(s), and performing one or more of liquid chromatography (LC), gas chromatography (GC), Fourier transform infrared (FTIR) spectroscopy, Raman spectroscopy, mass spectrometry (MS) and/or nuclear magnetic resonance (NMR) spectroscopy.

In some embodiments, the subject invention can be used for reducing the number of carbon credits used by an operator involved in, e.g., agriculture, livestock production, forestry/reforestation, and pasture management. In some embodiments, the subject invention can be used for "carbon farming," where plants are grown for the non-commercial purpose of sequestering carbon in tracts of land.

Modes of Application

As used herein, "applying" a composition or product to a site refers to contacting a composition or product with a site such that the composition or product can have an effect on that site. The effect can be due to, for example, microbial growth and colonization, and/or the action of a metabolite, enzyme, biosurfactant or other microbial growth by-product. The mode of application depends upon the formulation of the composition, and can include, for example, spraying, pouring, sprinkling, injecting, spreading, mixing, dunking, fogging and misting. Formulations can include, for example, liquids, dry and/or wettable powders, flowable powders, dusts, granules, pellets, emulsions, microcapsules, steaks, oils, gels, pastes and/or aerosols. In an exemplary embodiment, the composition is applied after the composition has been prepared by, for example, dissolving the composition in water.

In one embodiment, the site to which the composition is applied is the soil (or rhizosphere) in which plants will be planted or are growing (e.g., a crop, a field, an orchard, a grove, a pasture/prairie or a forest). The compositions of the subject invention can be pre-mixed with irrigation fluids, wherein the compositions percolate through the soil and can be delivered to, for example, the roots of plants to influence the root microbiome.

In one embodiment, the compositions are applied to soil surfaces, with or without water, where the beneficial effect of the soil application can be activated by rainfall, sprinkler, flood, or drip irrigation.

In one embodiment, the site is a plant or plant part. The composition can be applied directly thereto as a seed treatment, or to the surface of a plant or plant part (e.g., to the surface of the roots, tubers, stems, flowers, leaves, fruit, or flowers). In a specific embodiment, the composition is contacted with one or more roots of the plant. The composition can be applied directly to the roots, e.g., by spraying or dunking the roots, and/or indirectly, e.g., by administering the composition to the soil in which the plant grows (or the rhizosphere). The composition can be applied to the seeds of the plant prior to or at the time of planting, or to any other part of the plant and/or its surrounding environment.

In one embodiment, wherein the method is used in a large scale setting, such as in a citrus grove, a pasture or prairie, a forest, a sod or turf farm, or an agricultural crop, the method can comprise administering the composition into a tank connected to an irrigation system used for supplying water, fertilizers, pesticides or other liquid compositions. Thus, the plant and/or soil surrounding the plant can be treated with the composition via, for example, soil injection, soil drenching, using a center pivot irrigation system, with a spray over the seed furrow, with micro-jets, with drench sprayers, with boom sprayers, with sprinklers and/or with drip irrigators. Advantageously, the method is suitable for treating hundreds of acres of land.

In one embodiment, wherein the method is used in a smaller scale setting, such as in a home garden or greenhouse, the method can comprise pouring the composition (mixed with water and other optional additives) into the tank of a handheld lawn and garden sprayer and spraying soil or another site with the composition. The composition can also be mixed into a standard handheld watering can and poured onto a site.

Plants and/or their environments can be treated at any point during the process of cultivating the plant. For example, the composition can be applied to the soil prior to, concurrently with, or after the time when seeds are planted therein. It can also be applied at any point thereafter during the development and growth of the plant, including when the plant is flowering, fruiting, and during and/or after abscission of leaves.

In one embodiment, the methods and compositions according to the subject invention lead to an increase in one or more of: root mass, stalk diameter, plant height, canopy density, chlorophyll content, flower count, bud count, bud size, bud density, leaf surface area, and/or nutrient uptake of a plant, by at least 1%, 5%, 10%, 20%, 30%, 40%, 50%, 60% 70%, 80%, 90%, 100%, 150%, 200%, or more, compared to a plant growing in an untreated environment.

In one embodiment, the methods and compositions according to the subject invention lead to an increase in suberin, cutin, cutan and/or lignin accumulation in a plant and/or in soil, by at least 1%, 5%, 10%, 20%, 30%, 40%, 50%, 60% 70%, 80%, 90%, 100%, 150%, 200%, or more, compared to untreated plants and/or soil.

In one embodiment, the methods and compositions according to the subject invention lead to an increase in soil carbon content by at least 1%, 5%, 10%, 20%, 30%, 40%, 50%, 60% 70%, 80%, 90%, 100%, 150%, 200%, or more, compared to untreated soil.

Target Plants

As used here, the term "plant" includes, but is not limited to, any species of woody, ornamental or decorative, crop or cereal, fruit plant or vegetable plant, flower or tree, macroalga or microalga, phytoplankton and photosynthetic algae (e.g., green algae *Chlamydomonas reinhardtii*). "Plant" also includes a unicellular plant (e.g. microalga) and a plurality of plant cells that are largely differentiated into a colony (e.g. volvox) or a structure that is present at any stage of a plant's development. Such structures include, but are not limited to, a fruit, a seed, a shoot, a stem, a leaf, a root, a flower petal, etc. Plants can be standing alone, for example, in a garden, or can be one of many plants, for example, as part of an orchard, crop or pasture.

As used herein, "crop plants" refer to any species of plant or alga, grown for profit and/or for sustenance for humans, animals or aquatic organisms, or used by humans (e.g., textile, cosmetics, and/or drug production), or viewed by humans for pleasure (e.g., flowers or shrubs in landscaping or gardens) or any plant or alga, or a part thereof, used in industry, commerce or education. Crop plants can be plants that can be obtained by traditional breeding and optimization methods or by biotechnological and recombinant methods, or combinations of these methods, including the transgenic plants and the plant varieties.

Types of crop plants that can benefit from application of the products and methods of the subject invention include, but are not limited to: row crops (e.g., corn, soy, sorghum, peanuts, potatoes, etc.), field crops (e.g., alfalfa, wheat, grains, etc.), tree crops (e.g., walnuts, almonds, pecans, hazelnuts, pistachios, etc.), citrus crops (e.g., orange, lemon, grapefruit, etc.), fruit crops (e.g., apples, pears, strawberries, blueberries, blackberries, etc.), turf crops (e.g., sod), ornamentals crops (e.g., flowers, vines, etc.), vegetables (e.g., tomatoes, carrots, etc.), vine crops (e.g., grapes, etc.), forestry (e.g., pine, spruce, eucalyptus, poplar, etc.), managed pastures (any mix of plants used to support grazing animals).

Additional examples of plants for which the subject invention is useful include, but are not limited to, cereals and grasses (e.g., wheat, barley, rye, oats, rice, maize, sorghum, corn), beets (e.g., sugar or fodder beets); fruit (e.g., grapes, strawberries, raspberries, blackberries, pomaceous fruit, stone fruit, soft fruit, apples, pears, plums, peaches, almonds, cherries or berries); leguminous crops (e.g., beans, lentils, peas or soya); oil crops (e.g., oilseed rape, mustard, poppies, olives, sunflowers, coconut, castor, cocoa or ground nuts); cucurbits (e.g., pumpkins, cucumbers, squash or melons); fiber plants (e.g., cotton, flax, hemp or jute); citrus fruit (e.g., oranges, lemons, grapefruit or tangerines); vegetables (e.g., spinach, lettuce, asparagus, cabbages, carrots, onions, tomatoes, potatoes or bell peppers); Lauraceae (e.g., avocado, Cinnamonium or camphor); and also tobacco, nuts, herbs, spices, medicinal plants, coffee, eggplants, sugarcane, tea, pepper, grapevines, hops, the plantain family, latex plants, cut flowers and ornamentals.

In certain embodiments, the crop plant is a citrus plant. Examples of citrus plants according to the subject invention include, but are not limited to, orange trees, lemon trees, lime trees and grapefruit trees. Other examples include *Citrus maxima* (Pomelo), *Citrus medica* (Citron), *Citrus micrantha* (Papeda), *Citrus reticulata* (Mandarin orange), *Citrus paradisi* (grapefruit), *Citrus japonica* (kumquat), *Citrus australasica* (Australian Finger Lime), *Citrus australis* (Australian Round lime), *Citrus glauca* (Australian Desert Lime), *Citrus garrawayae* (Mount White Lime), *Citrus gracilis* (Kakadu Lime or Humpty Doo Lime), *Citrus inodora* (Russel River Lime), *Citrus warburgiana* (New Guinea Wild Lime), *Citrus wintersii* (Brown River Finger Lime), *Citrus halimii* (limau kadangsa, limau kedut kera), *Citrus indica* (Indian wild orange), *Citrus macroptera*, and *Citrus latipes, Citrus* x *aurantiifolia* (Key lime), *Citrus* x *aurantium* (Bitter orange), *Citrus* x *latifolia* (Persian lime), *Citrus* x *limon* (Lemon), *Citrus* x *limonia* (Rangpur), *Citrus* x *sinensis* (Sweet orange), *Citrus* x *tangerina* (Tangerine), Imperial lemon, tangelo, orangelo, tangor, kinnow, kiyomi, Minneola tangelo, oroblanco, ugli, Buddha's hand, citron, bergamot orange, blood orange, calamondin, clementine, Meyer lemon, and yuzu.

In some embodiments, the crop plant is a relative of a citrus plant, such as orange jasmine, limeberry, and trifoliate orange (*Citrus trifolata*).

Additional examples of target plants include all plants that belong to the superfamily Viridiplantae, in particular monocotyledonous and dicotyledonous plants including fodder or forage legumes, ornamental plants, food crops, trees or shrubs selected from *Acer* spp., *Actinidia* spp., *Abelmoschus* spp., *Agave sisalana*, *Agropyron* spp., *Agrostis stolonifera*, *Allium* spp., *Amaranthus* spp., *Ammophila arenaria*, *Ananas comosus*, *Annona* spp., *Apium graveolens*, *Arachis* spp., *Artocarpus* spp., *Asparagus officinalis*, *Avena* spp. (e.g., *A. sativa*, *A. fatua*, *A. byzantina*, *A. fatua* var. *sativa*, *A. hybrida*), *Averrhoa carambola*, *Bambusa* sp., *Benincasa hispida*, *Bertholletia excelsea*, *Beta vulgaris*, *Brassica* spp. (e.g., *B. napus*, *B. rapa* ssp. [canola, oilseed rape, turnip rape]), *Cadaba farinosa*, *Camellia sinensis*, *Canna indica*, *Cannabis sativa*, *Capsicum* spp., *Carex elata*, *Carica papaya*, *Carissa macrocarpa*, *Carya* spp., *Carthamus tinctorius*, *Castanea* spp., *Ceiba pentandra*, *Cichorium endivia*, *Cinnamomum* spp., *Citrullus lanatus*, *Citrus* spp., *Cocos* spp., *Coffea* spp., *Colocasia esculenta*, *Cola* spp., *Corchorus* sp., *Coriandrum sativum*, *Corylus* spp., *Crataegus* spp., *Crocus sativus*, *Cucurbita* spp., *Cucumis* spp., *Cynara* spp., *Daucus carota*, *Desmodium* spp., *Dimocarpus longan*, *Dioscorea* spp., *Diospyros* spp., *Echinochloa* spp., *Elaeis* (e.g., *E. guineensis*, *E. oleifera*), *Eleusine coracana*, *Eragrostis tef*, *Erianthus* sp., *Eriobotrya japonica*, *Eucalyptus* sp., *Eugenia uniflora*, *Fagopyrum* spp., *Fagus* spp., *Festuca arundinacea*, *Ficus carica*, *Fortunella* spp., *Fragaria* spp., *Ginkgo biloba*, *Glycine* spp. (e.g., *G. max*, *Soja hispida* or *Soja max*), *Gossypium hirsutum*, *Helianthus* spp. (e.g., *H. annuus*), *Hemerocallis fulva*, *Hibiscus* spp., *Hordeum* spp. (e.g., *H. vulgare*), *Ipomoea batatas*, *Juglans* spp., *Lactuca saliva*, *Lathyrus* spp., *Lens culinaris*, *Linum usitatissimum*, *Litchi chinensis*, *Lotus* spp., *Luffa acutangula*, *Lupinus* spp., *Luzula sylvatica*, *Lycopersicon* spp. (e.g., *L. esculentum*, *L. lycopersicum*, *L. pyriforme*), *Macrotyloma* spp., *Malus* spp., *Malpighia emarginata*, *Mammea americana*, *Mangifera indica*, *Manihot* spp., *Manilkara zapota*, *Medicago sativa*, *Melilotus* spp., *Mentha* spp., *Miscanthus sinensis*, *Momordica* spp., *Morus nigra*, *Musa* spp., *Nicotiana* spp., *Olea* spp., *Opuntia* spp., *Ornithopus* spp., *Oryza* spp. (e.g., *O. sativa*, *O. latifolia*), *Panicum miliaceum*, *Panicum virgatum*, *Passiflora edulis*, *Pastinaca saliva*, *Pennisetum* sp., *Persea* spp., *Petroselinum crispum*, *Phalaris arundinacea*, *Phaseolus* spp., *Phleum pratense*, *Phoenix* spp., *Phragmites australis*, *Physalis* spp., *Pinus* spp., *Pistacia vera*, *Pisum* spp., *Poa* spp., *Populus* spp., *Prosopis* spp., *Prunus* spp., *Psidium* spp., *Punica granatum*, *Pyrus communis*, *Quercus* spp. (e.g., *Q. suber* L), *Raphanus sativus*, *Rheum rhabarbarum*, *Ribes* spp., *Ricinus communis*, *Rubus* spp., *Saccharum* spp., *Salix* sp., *Sambucus* spp., *Secale cereale*, *Sesamum* spp., *Sinapis* sp., *Solanum* spp. (e.g., *S. tuberosum*, *S. integrifolium* or *S. lycopersicum*), *Sorghum bicolor*, *Spinacia* spp., *Syzygium* spp., *Tagetes* spp., *Tamarindus indica*, *Theobroma cacao*, *Trifolium* spp., *Tripsacum dactyloides*, *Triticosecale rimpaui*, *Triticum* spp. (e.g., *T. aestivum*, *T. durum*, *T. turgidum*, *T. hybernum*, *T. macha*, *T. sativum*, *T. monococcum* or *T. vulgare*), *Tropaeolum minus*, *Tropaeolum majus*, *Vaccinium* spp., *Vicia* spp., *Vigna* spp., *Viola odorata*, *Vitis* spp., *Zea mays*, *Zizania palustris*, *Ziziphus* spp., amongst others.

Target plants can also include, but are not limited to, corn (*Zea mays*), *Brassica* sp. (e.g., *B. napus*, *B. rapa*, *B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Target vegetable plants include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Target turfgrasses include, but are not limited to: annual bluegrass (*Poa annua*); annual ryegrass (*Lolium multiflorum*); Canada bluegrass (*Poa compressa*); Chewings fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerate*); perennial ryegrass (*Lolium perenne*); red fescue (*Festuca rubra*); redtop (*Agrostis alba*); rough bluegrass (*Poa trivialis*); sheep fescue (*Festuca ovine*); smooth bromegrass (*Bromus inermis*); tall fescue (*Festuca arundinacea*); timothy (*Phleum pretense*); velvet bentgrass (*Agrostis canine*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Further plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive etc. Leguminous plants include beans and peas. Beans include guar, locust bean, fenugreek, soybean, garden beans, cowpea, mungbean, lima bean, fava bean, lentils, chickpea, etc. Further plants of interest include Cannabis (e.g., saliva, indica, and ruderalis) and industrial hemp.

In certain specific embodiments, the plant is a woody tree, such as a cork tree (*Q. suber*). In other embodiments, the plant is a potato.

In some embodiments, the plant has been genetically modified to produce suberin and/or other degradation-resistant organic polymers disclosed herein in enhanced amounts, e.g., in amounts that are at least 1%, 5%, 10%, 20%, 50%, 75%, or at least 95% greater than wild-type and/or standard crop plants. Thus, in certain embodiments, the plants treated according to the subject invention are suberin "over-producers."

All plants and plant parts can be treated in accordance with the invention. In this context, plants are understood as meaning all plants and plant populations such as desired and undesired wild plants or crop plants (including naturally occurring crop plants). Crop plants can be plants that can be obtained by traditional breeding and optimization methods or by biotechnological and recombinant methods, or combinations of these methods, including the transgenic plants and the plant varieties.

Plant tissue and/or plant parts are understood as meaning all aerial and subterranean parts and organs of the plants such as shoots, leaves, flowers, roots, needles, stalks, stems, fruits, seeds, tubers and rhizomes. The plant parts also include crop material and vegetative and generative propagation material, for example cuttings, tubers, rhizomes, slips and seeds.

Compositions

In one embodiment, the subject invention provides compositions comprising one or more microorganisms and/or microbial growth by-products, wherein the one or more microorganisms are beneficial, non-pathogenic, soil-colonizing microorganisms. The composition can be used for reducing greenhouse gases via, for example, improved plant carbon utilization and storage and/or enhanced sequestration of carbon in soil. In some embodiments, the composition comprises one or more microbes that can also be useful for enhancing rhizosphere properties, enhancing plant biomass and/or enhancing accumulation of carbon-rich, degradation-resistant molecules in plant tissue and soil.

In preferred embodiments, the microbial growth by-products are biosurfactants and/or enzymes, although other metabolites may also be present in the composition.

Advantageously, in preferred embodiments, the microbe-based compositions according to the subject invention are non-toxic and can be applied in high concentrations without causing irritation to, for example, the skin or digestive tract of a human or other non-pest animal. Thus, the subject invention is particularly useful where application of the microbe-based compositions occurs in the presence of living organisms, such as growers and livestock.

In one embodiment, multiple microorganisms can be used together, where the microorganisms create a synergistic benefit towards accumulation of degradation-resistant molecules in plant tissue and soil.

The species and ratio of microorganisms and other ingredients in the composition can be customized and optimized for specific local conditions at the time of application, such as, for example, which soil type, plant and/or crop is being treated; what season, climate and/or time of year it is when a composition is being applied; and what mode and/or rate of application is being utilized. Thus, the composition can be customizable for any given site.

The microorganisms useful according to the subject invention can be, for example, non-plant-pathogenic strains of bacteria, yeast and/or fungi. These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frame-shift mutation or repeat expansion) as compared to the reference microorganism. Procedures for making mutants are well known in the microbiological art. For example, UV mutagenesis and nitrosoguanidine are used extensively toward this end.

In one embodiment, the microorganism is a yeast or fungus. Yeast and fungus species suitable for use according to the current invention, include *Aureobasidium* (e.g., *A. pullulans*), *Blakeslea*, *Candida* (e.g., *C. apicola, C. bombicola, C. nodaensis*), *Cryptococcus*, *Debaryomyces* (e.g., *D. hansenii*), *Entomophthora*, *Hanseniaspora*, (e.g., *H. uvarum*), *Hansenula*, *Issatchenkia*, *Kluyveromyces* (e.g., *K. phaffii*), *Lentinula edodes*, *Mortierella*, mycorrhizal fungi, *Meyerozyma* (*M. guilliermondii, M caribica*), *Penicillium*, *Phycomyces*, *Pichia* (e.g., *P. anomala, P. guilliermondii, P. occidentalis, P. kudriavzevii*), *Pleurotus* (e.g., *P. ostreatus*), *Pseudozyma* (e.g., *P. aphidis*), *Saccharomyces* (e.g., *S. boulardii sequela, S. cerevisiae, S. torula*), *Starmerella* (e.g., *S. bombicola*), *Torulopsis*, *Trichoderma* (e.g., *T. guizhouse, T. reesei, T. harzianum, T. koningii, T. hamatum, T. viride*), *Ustilago* (e.g., *U. maydis*), *Wickerhamomyces* (e.g., *W. anomalus*), *Williopsis* (e.g., *W. mrakii*), *Zygosaccharomyces* (e.g., *Z. bailii*), and others.

In certain embodiments, the microorganisms are bacteria, including Gram-positive and Gram-negative bacteria. The bacteria may be, for example *Agrobacterium* (e.g., *A. radiobacter*), *Azotobacter* (*A. vinelandii, A. chroococcum*), *Azospirillum* (e.g., *A. brasiliensis*), *Bacillus* (e.g., *B. amyloliquefaciens, B. circulans, B. firmus, B. laterosporus, B. licheniformis, B. megaterium, B. mucilaginosus, B. polymyxa, B. subtilis, Brevibacillus laterosporus*), *Frateuria* (e.g., *F. aurantia*), *Microbacterium* (e.g., *M. laevaniformans*), myxobacteria (e.g., *Myxococcus xanthus, Stignatella aurantiaca, Sorangium cellulosum, Minicystis rosea*), *Paenibacillus polymyxa*, *Pantoea* (e.g., *P. agglomerans*), *Pseudomonas* (e.g., *P. aeruginosa, P. chlororaphis* subsp. *aureofaciens* (Kluyver), *P. putida*), *Rhizobium* spp., *Rhodospirillum* (e.g., *R. rubrum*), *Sphingomonas* (e.g., *S. paucimobilis*), and/or *Thiobacillus thiooxidans* (*Acidothiobacillus thiooxidans*).

In certain embodiments, the microorganism is one that is capable of fixing and/or solubilizing nitrogen, potassium, phosphorous and/or other micronutrients in soil.

In one embodiment, the microorganism is a nitrogen-fixing microorganism, or a diazotroph, selected from species of, for example, *Azospirillum, Azotobacter, Chlorobiaceae, Cyanothece, Frankia, Klebsiella, rhizobia, Bacillus, Trichodesmium, Meyerozyma* and some Archaea. In one embodiment, the nitrogen-fixing microbe is *Azotobacter vinelandii*. In one embodiment, *Bacillus amyloliquefaciens* NRRL B-67928 and/or *Bacillus subtilis* B4 NRRL B-68031 are the nitrogen-fixing microbe(s).

In one embodiment, the microorganism is a potassium-mobilizing microorganism, or KMB, selected from, for example, *Bacillus mucilaginosus, Frateuria aurantia* or *Glomus mosseae*. In one embodiment, the potassium-mobilizing microorganism is *Frateuria aurantia*. In one embodiment, the potassium-mobilizing microorganism is *Wickerhamomyces anomalus* NRRL Y-68030.

In one embodiment, the microorganism is a non-denitrifying microorganism capable of converting nitrous oxide from the atmosphere into nitrogen in the soil, such as, for example, *Dyadobacter fermenters*.

In one embodiment, a combination of microorganisms is used in the subject microbe-based composition, wherein the microorganisms work synergistically with one another to enhance plant biomass, and/or to enhance the properties of the rhizosphere.

In specific exemplary embodiments, the microbes utilized according to the subject invention are selected from one or more of: *Trichoderma* spp. (e.g., *T. harzianum, T. viride, T koningii*, and *T. guizhouse*); *Bacillus* spp. (e.g., *B. amyloliquefaciens, B. subtilis, B. megaterium, B. polymyxa, B. licheniformis*, and Brevibacillus laterosporus); *Meyerozyma guilliermondii; Pichia occidentalis; Wickerhamomyces anomalus;* and *Debaryomyces hansenii*.

In one specific embodiment, the composition comprises *B. amyloliquefaciens* and a *Trichoderma* sp., such as, for example, *T. harzianum* T-22 and/or *T. guizhouse*.

In one embodiment, the composition comprises *B. amyloliquefaciens* NRRL B-67928 "*B. amy.*" A culture of the *B. amyloliquefaciens* "*B. amy*" microbe has been deposited with the Agricultural Research Service Northern Regional Research Laboratory (NRRL), 1400 Independence Ave., S.W., Washington, DC, 20250, USA. The deposit has been assigned accession number NRRL B-67928 by the depository and was deposited on Feb. 26, 2020.

The deposited *B. amyloliquefaciens* NRRL B-67928 is viable, commercially available, reproducible, and all restrictions on the availability of the deposit to the public will be irrevocably removed upon the granting of the patent. p In one embodiment, the composition comprises *B. subtilis* NRRL B-68031 "B4." A culture of the B4 microbe has been deposited with the Agricultural Research Service Northern Regional Research Laboratory (NRRL) Culture Collection, 1815 N. University St., Peoria, IL, USA. The deposit has been assigned accession number NRRL B-68031 by the depository and was deposited on May 6, 2021.

In one embodiment, the composition comprises *Wickerhamomyces anomalus* NRRL Y-68030. A culture of this microbe has been deposited with the Agricultural Research Service Northern Regional Research Laboratory (NRRL) Culture Collection, 1815 N. University St., Peoria, IL, USA. The deposit has been assigned accession number NRRL Y-68030 by the depository and was deposited on May 6, 2021.

Each of the subject cultures has been deposited under conditions that assure that access to the culture will be available during the pendency of this patent application to one determined by the Commissioner of Patents and Trademarks to be entitled thereto under 37 CFR 1.14 and 35 U.S.C 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

In a specific embodiment, the concentration of each microorganism included in the composition is $1\times10^6$ to $1\times10^{13}$ CFU/g, $1\times10^7$ to $1\times10^{12}$ CFU/g, $1\times10^8$ to $1\times10^{11}$ CFU/g, or $1\times10^9$ to $1\times10^{10}$ CFU/g of the composition.

In one embodiment, the total microbial cell concentration of the composition is at least $1\times10^6$ CFU/g, including up to $1\times10^9$ CFU/g, $1\times10^{10}$, $1\times10^{11}$, $1\times10^{12}$ and/or $1\times10^{13}$ or more CFU/g. In one embodiment, the microorganisms of the subject composition comprise about 5 to 20% of the total composition by weight, or about 8 to 15%, or about 10 to 12%.

The composition can comprise the leftover fermentation substrate and/or purified or unpurified growth by-products, such as enzymes, biosurfactants and/or other metabolites. The microbes can be live or inactive.

The microbes and microbe-based compositions of the subject invention have a number of beneficial properties that are useful for, e.g., increasing plant biomass and/or enhancing accumulation of degradation-resistant organic polymers. For example, the compositions can comprise products resulting from the growth of the microorganisms, such as biosurfactants, proteins and/or enzymes, either in purified or crude form. Furthermore, the microorganisms can enhance plant growth, induce auxin production, enable solubilization, absorption and/or balance of nutrients in the soil, and protect plants from pests and pathogens.

In one embodiment, the microorganisms of the subject composition are capable of producing a biosurfactant. In another embodiment, biosurfactants can be produced separately by other microorganisms and added to the composition, either in purified form or in crude form. Crude form biosurfactants can comprise, for example, biosurfactants and other products of cellular growth in the leftover fermentation medium resulting from cultivation of a biosurfactant-producing microbe. This crude form biosurfactant composition can comprise from about 0.001% to about 90%, about 25% to about 75%, about 30% to about 70%, about 35% to about 65%, about 40% to about 60%, about 45% to about 55%, or about 50% pure biosurfactant.

Biosurfactants form an important class of secondary metabolites produced by a variety of microorganisms such as bacteria, fungi, and yeasts. As amphiphilic molecules, microbial biosurfactants reduce the surface and interfacial tensions between the molecules of liquids, solids, and gases. Furthermore, the biosurfactants according to the subject invention are biodegradable, have low toxicity, are effective in solubilizing and degrading insoluble compounds in soil and can be produced using low cost and renewable resources. They can inhibit adhesion of undesirable microorganisms to a variety of surfaces, prevent the formation of biofilms, and can have powerful emulsifying and demulsifying properties. Furthermore, the biosurfactants can also be used to improve wettability and to achieve even solubilization and/or distribution of fertilizers, nutrients, and water in the soil.

Biosurfactants according to the subject methods can be selected from, for example, low molecular weight glycolipids (e.g., sophorolipids, cellobiose lipids, rhamnolipids, mannosylerythritol lipids and trehalose lipids), lipopeptides (e.g., surfactin, iturin, fengycin, arthrofactin and lichenysin), flavolipids, phospholipids (e.g., cardiolipins), fatty acid esters, and high molecular weight polymers such as lipoproteins, lipopolysaccharide-protein complexes, and polysaccharide-protein-fatty acid complexes.

The composition can comprise one or more biosurfactants at a concentration of 0.001% to 10%, 0.01% to 5%, 0.05% to 2%, and/or from 0.1% to 1% by weight.

The composition can comprise the fermentation medium containing a live and/or an inactive culture, the purified or crude form growth by-products, such as biosurfactants, enzymes, and/or other metabolites, and/or any residual nutrients.

The product of fermentation may be used directly, with or without extraction or purification. If desired, extraction and purification can be easily achieved using standard extraction and/or purification methods or techniques described in the literature.

The microorganisms in the composition may be in an active or inactive form, or in the form of vegetative cells, reproductive spores, mycelia, hyphae, conidia or any other form of microbial propagule. The composition may also contain a combination of any of these microbial forms.

In one embodiment, when a combination of strains of microorganism are included in the composition, the different strains of microbe are grown separately and then mixed together to produce the composition.

Advantageously, in accordance with the subject invention, the composition may comprise the medium in which the microbes were grown. The composition may be, for example, at least, by weight, 1%, 5%, 10%, 25%, 50%, 75%, or 100% growth medium. The amount of biomass in the composition, by weight, may be, for example, anywhere from 0% to 100% inclusive of all percentages therebetween.

In one embodiment, the composition is preferably formulated for application to soil, seeds, whole plants, or plant parts (including, but not limited to, roots, tubers, stems, flowers and leaves). In certain embodiments, the composition is formulated as, for example, liquid, dust, granules, microgranules, pellets, wettable powder, flowable powder, emulsions, microcapsules, oils, or aerosols.

To improve or stabilize the effects of the composition, it can be blended with suitable adjuvants and then used as such or after dilution, if necessary. In preferred embodiments, the composition is formulated as a liquid, a concentrated liquid, or as dry powder or granules that can be mixed with water and other components to form a liquid product. In one embodiment, the composition can comprise glucose (e.g., in the form of molasses), in addition to an osmoticum substance, to ensure optimum osmotic pressure during storage and transport of the dry product.

The compositions can be used either alone or in combination with other compounds and/or methods for efficiently enhancing plant health, growth and/or yields, and/or for supplementing the growth of the microorganisms in the composition. For example, in one embodiment, the composition can include and/or can be applied concurrently with nutrients and/or micronutrients for enhancing plant and/or microbe growth, such as magnesium, phosphate, nitrogen, potassium, selenium, calcium, sulfur, iron, copper, and zinc; and/or one or more prebiotics, such as biochar, kelp extract, fulvic acid, chitin, humate and/or humic acid. The exact materials and the quantities thereof can be determined by a grower or an agricultural scientist having the benefit of the subject disclosure.

The compositions can also be used in combination with other agricultural compounds and/or crop management systems. In one embodiment, the composition can optionally comprise, or be applied with, for example, natural and/or chemical pesticides, repellants, herbicides, fertilizers, water treatments, non-ionic surfactants and/or soil amendments. Preferably, however, the composition does not comprise and/or is not used with benomyl, dodecyl dimethyl ammonium chloride, hydrogen dioxide/peroxyacetic acid, imazilil, propiconazole, tebuconazole, or triflumizole.

If the composition is mixed with compatible chemical additives, the chemicals are preferably diluted with water prior to addition of the subject composition.

Further components can be added to the composition, for example, buffering agents, carriers, other microbe-based compositions produced at the same or different facility, viscosity modifiers, preservatives, nutrients for microbe growth, tracking agents, biocides, other microbes, surfactants, emulsifying agents, lubricants, solubility controlling agents, pH adjusting agents, preservatives, stabilizers and ultra-violet light resistant agents.

The pH of the microbe-based composition should be suitable for the microorganism of interest. In a preferred embodiment, the pH of the composition is about 3.5 to 7.0, about 4.0 to 6.5, or about 5.0.

Optionally, the composition can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C.

The microbe-based compositions may be used without further stabilization, preservation, and storage, however. Advantageously, direct usage of these microbe-based compositions preserves a high viability of the microorganisms, reduces the possibility of contamination from foreign agents and undesirable microorganisms, and maintains the activity of the by-products of microbial growth.

In other embodiments, the composition (microbes, growth medium, or microbes and medium) can be placed in containers of appropriate size, taking into consideration, for example, the intended use, the contemplated method of application, the size of the fermentation vessel, and any mode of transportation from microbe growth facility to the location of use. Thus, the containers into which the microbe-based composition is placed may be, for example, from 1 pint to 1,000 gallons or more. In certain embodiments the containers are 1 gallon, 2 gallons, 5 gallons, 25 gallons, or larger.

The subject compositions can be used either alone or in combination with other compounds for efficient enhancement of plant health, growth and/or yields, as well as other compounds for efficient treatment and prevention of plant pathogenic pests. For example, the methods can be used concurrently with sources of nutrients and/or micronutrients for enhancing plant and/or microbe growth, such as magnesium, phosphate, nitrogen, potassium, selenium, calcium, sulfur, iron, copper, and zinc; and/or one or more prebiotics, such as kelp extract, fulvic acid, chitin, humate and/or humic acid. The exact materials and the quantities thereof can be determined by a grower or an agricultural scientist having the benefit of the subject disclosure.

In one embodiment, the composition comprises and/or is applied concurrently with biochar, or charcoal that is produced by, for example, pyrolysis of crop waste and other biomass in the absence of oxygen. In certain embodiments, biochar acts synergistically with the microorganisms of the soil treatment composition, providing an additional soil carbon source and facilitating the solubilization of nutrients, growth of larger roots, and growth of more robust plant biomass. In some embodiments, the biochar can adsorb and desorb fertilizer, thereby providing a slow-release application and reducing risk of leaching and denitrification before plant uptake.

The compositions can also be used in combination with other agricultural compounds and/or crop management systems. In one embodiment, the composition can optionally comprise, and/or be applied with, for example, natural and/or chemical pesticides, repellants, herbicides, fertilizers, water treatments, non-ionic surfactants and/or soil amendments.

In one embodiment, the subject compositions are compatible for use with agricultural compounds characterized as antiscalants, such as, e.g., hydroxyethylidene diphosphonic acid;

bactericides, such as, e.g., streptomycin sulfate and/or Galltrol® (*A. radiobacter* strain K84);

biocides, such as, e.g., chlorine dioxide, didecyldimethyl ammonium chloride, halogenated heterocyclic, and/or hydrogen dioxide/peroxyacetic acid;

fertilizers, such as, e.g., N-P-K fertilizers, calcium ammonium nitrate 17-0-0, potassium thiosulfate, nitrogen (e.g., 10-34-0, Kugler KQ-XRN, Kugler KS-178C, Kugler KS-2075, Kugler LS 6-24-6S, UN 28, UN 32), and/or potassium;

fungicides, such as, e.g., chlorothalonil, manicozeb hexamethylenetetramine, aluminum tris, azoxystrobin, *Bacillus* spp. (e.g., *B. licheniformis* strain 3086, *B. subtilis, B. subtilis* strain QST 713), benomyl, boscalid, pyraclostrobin, captan, carboxin, chloroneb, chlorothalonil, copper culfate, cyazofamid, dicloran, dimethomorph, etridiazole, thiophanate-methyl, fenamidone, fenarimol, fludioxonil, fluopicolide, flutolanil, iprodione, mancozeb, maneb, mefanoxam, fludioxonil, mefenoxam, metalaxyl, myclobutanil, oxathiapiprolin, pentachloronitrobenzene (quintozene), phosphorus acid, propamocarb, propanil, pyraclostrobin, *Reynoutria sachalinensis, Streptomyces* spp. (e.g., *S. griseoviridis* strain K61, *S. lydicus* WYEC 108), sulfur, urea, thiabendazole, thiophanate methyl, thiram, triadimefon, triadimenol, and/or vinclozolin;

growth regulators, such as, e.g., ancymidol, chlormequat chloride, diaminozide, paclobutrazol, and/or uniconazole;

herbicides, such as, e.g., glyphosate, oxyfluorfen, and/or pendimethalin;

insecticides, such as, e.g., acephate, azadirachtin, *B. thuringiensis* (e.g., subsp. *israelensis* strain AM 65-52), *Beauveria bassiana* (e.g., strain GHA), carbaryl, chlorpyrifos, cyantraniliprole, cyromazine, dicofol, diazinon, dinotefuran, imidacloprid, *Isaria fumosorosae* (e.g., Apopka strain 97), lindane, and/or malathion;

water treatments, such as, e.g., hydrogen peroxide (30-35%), phosphonic acid (5-20%), and/or sodium chlorite;

as well as glycolipids, lipopeptides, deet, diatomaceous earth, citronella, essential oils, mineral oils, garlic extract, chili extract, and/or any known commercial and/or home-made pesticide that is determined to be compatible by the skilled artisan having the benefit of the subject disclosure.

Preferably, the composition does not comprise and/or is not applied simultaneously with, or within 7 to 10 days before or after, application of the following compounds: benomyl, dodecyl dimethyl ammonium chloride, hydrogen dioxide/peroxyacetic acid, imazilil, propiconazole, tebuconazole, or triflumizole.

In certain embodiments, the compositions and methods can be used to enhance the effectiveness of other compounds, for example, by enhancing the penetration of a pesticidal compound into a plant or pest, or enhancing the bioavailability of a nutrient to plant roots. The microbe-based products can also be used to supplement other treatments, for example, antibiotic treatments. Advantageously, the subject invention helps reduce the amount of antibiotics that must be administered to a crop or plant in order to be effective at treating and/or preventing bacterial infection.

Growth of Microbes According to the Subject Invention

The subject invention utilizes methods for cultivation of microorganisms and production of microbial metabolites and/or other by-products of microbial growth. The subject invention further utilizes cultivation processes that are suitable for cultivation of microorganisms and production of microbial metabolites on a desired scale. These cultivation processes include, but are not limited to, submerged cultivation/fermentation, solid state fermentation (SSF), and modifications, hybrids and/or combinations thereof.

As used herein "fermentation" refers to cultivation or growth of cells under controlled conditions. The growth could be aerobic or anaerobic. In preferred embodiments, the microorganisms are grown using SSF and/or modified versions thereof.

In one embodiment, the subject invention provides materials and methods for the production of biomass (e.g., viable cellular material), extracellular metabolites (e.g. small molecules and proteins), residual nutrients and/or intracellular components (e.g. enzymes and other proteins).

The microbe growth vessel used according to the subject invention can be any fermenter or cultivation reactor for industrial use. In one embodiment, the vessel may have functional controls/sensors or may be connected to functional controls/sensors to measure important factors in the cultivation process, such as pH, oxygen, pressure, temperature, humidity, microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of organisms in a sample. The technique can also provide an index by which different environments or treatments can be compared.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. In the case of submerged fermentation, the oxygenated air may be ambient air supplemented daily through mechanisms including impellers for mechanical agitation of liquid, and air spargers for supplying bubbles of gas to liquid for dissolution of oxygen into the liquid.

The method can further comprise supplementing the cultivation with a carbon source. The carbon source can be a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, canola oil, rice bran oil, olive oil, corn oil, sunflower oil, sesame oil, and/or linseed oil; etc. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, sodium chloride, calcium carbonate, and/or sodium carbonate. These inorganic salts may be used independently or in a combination of two or more.

In some embodiments, the method for cultivation may further comprise adding additional acids and/or antimicrobials in the medium before, and/or during the cultivation process. Antimicrobial agents or antibiotics are used for protecting the culture against contamination.

Additionally, antifoaming agents may also be added to prevent the formation and/or accumulation of foam during submerged cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the medium may be necessary.

The microbes can be grown in planktonic form or as biofilm. In the case of biofilm, the vessel may have within it a substrate upon which the microbes can be grown in a biofilm state. The system may also have, for example, the capacity to apply stimuli (such as shear stress) that encourages and/or improves the biofilm growth characteristics.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control undesirable bacterial growth.

In one embodiment, the subject invention further provides a method for producing microbial metabolites such as, for example, biosurfactants, enzymes, proteins, ethanol, lactic acid, beta-glucan, peptides, metabolic intermediates, polyunsaturated fatty acid, and lipids, by cultivating a microbe strain of the subject invention under conditions appropriate for growth and metabolite production; and, optionally, purifying the metabolite. The metabolite content produced by the method can be, for example, at least 20%, 30%, 40%, 50%, 60%, 70%, 80%, or 90%.

The microbial growth by-product produced by microorganisms of interest may be retained in the microorganisms or secreted into the growth medium. The medium may contain compounds that stabilize the activity of microbial growth by-product.

The biomass content of the fermentation medium may be, for example, from 5 g/l to 180 g/l or more, or from 10 g/l to 150 g/l.

The cell concentration may be, for example, at least $1 \times 10^6$ to $1 \times 10^{13}$, $1 \times 10^7$ to $1 \times 10^{12}$, $1 \times 10^8$ to $1 \times 10^{11}$, or $1 \times 10^9$ to $1 \times 10^{10}$ CFU/ml.

The method and equipment for cultivation of microorganisms and production of the microbial by-products can be performed in a batch, a quasi-continuous process, or a continuous process.

In one embodiment, all of the microbial cultivation composition is removed upon the completion of the cultivation (e.g., upon, for example, achieving a desired cell density, or density of a specified metabolite). In this batch procedure, an entirely new batch is initiated upon harvesting of the first batch.

In another embodiment, only a portion of the fermentation product is removed at any one time. In this embodiment, biomass with viable cells, spores, conidia, hyphae and/or mycelia remains in the vessel as an inoculant for a new cultivation batch. The composition that is removed can be a cell-free medium or contain cells, spores, or other reproductive propagules, and/or a combination of thereof. In this manner, a quasi-continuous system is created.

Advantageously, the method does not require complicated equipment or high energy consumption. The microorganisms of interest can be cultivated at small or large scale on site and utilized, even being still-mixed with their media.

Advantageously, the microbe-based products can be produced in remote locations. The microbe growth facilities may operate off the grid by utilizing, for example, solar, wind and/or hydroelectric power.

Preparation of Microbe-Based Products

One microbe-based product of the subject invention is simply the fermentation medium containing the microorganisms and/or the microbial metabolites produced by the microorganisms and/or any residual nutrients. The product of fermentation may be used directly without extraction or purification. If desired, extraction and purification can be easily achieved using standard extraction and/or purification methods or techniques described in the literature.

The microorganisms in the microbe-based products may be in an active or inactive form, or in the form of vegetative cells, reproductive spores, conidia, mycelia, hyphae, or any other form of microbial propagule. The microbe-based products may also contain a combination of any of these forms of a microorganism.

In one embodiment, different strains of microbe are grown separately and then mixed together to produce the microbe-based product. The microbes can, optionally, be blended with the medium in which they are grown and dried prior to mixing.

In one embodiment, the different strains are not mixed together, but are applied to a plant and/or its environment as separate microbe-based products.

The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

Upon harvesting the microbe-based composition from the growth vessels, further components can be added as the harvested product is placed into containers or otherwise transported for use. The additives can be, for example, buffers, carriers, other microbe-based compositions produced at the same or different facility, viscosity modifiers, preservatives, nutrients for microbe growth, surfactants, emulsifying agents, lubricants, solubility controlling agents, tracking agents, solvents, biocides, antibiotics, pH adjusting agents, chelators, stabilizers, ultra-violet light resistant agents, other microbes and other suitable additives that are customarily used for such preparations.

In one embodiment, buffering agents including organic and amino acids or their salts, can be added. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, potassium carbonate or bicarbonate, hydrochloric acid, nitric acid, sulfuric acid or a mixture.

The pH of the microbe-based composition should be suitable for the microorganism(s) of interest. In a preferred embodiment, the pH of the composition is about 3.5 to 7.0, about 4.0 to 6.5, or about 5.0.

In one embodiment, additional components such as an aqueous preparation of a salt, such as sodium bicarbonate or carbonate, sodium sulfate, sodium phosphate, sodium biphosphate, can be included in the formulation.

In certain embodiments, an adherent substance can be added to the composition to prolong the adherence of the product to plant parts. Polymers, such as charged polymers, or polysaccharide-based substances can be used, for example, xanthan gum, guar gum, levan, xylinan, gellan gum, curdlan, pullulan, dextran and others.

In preferred embodiments, commercial grade xanthan gum is used as the adherent. The concentration of the gum should be selected based on the content of the gum in the commercial product. If the xanthan gum is highly pure, then 0.001% (w/v—xanthan gum/solution) is sufficient.

In one embodiment, glucose, glycerol and/or glycerin can be added to the microbe-based product to serve as, for example, an osmoticum during storage and transport. In one embodiment, molasses can be included.

In one embodiment, prebiotics can be added to and/or applied concurrently with the microbe-based product to enhance microbial growth. Suitable prebiotics, include, for example, kelp extract, fulvic acid, chitin, humate and/or humic acid. In a specific embodiment, the amount of prebiotics applied is about 0.1 L/acre to about 0.5 L/acre, or about 0.2 L/acre to about 0.4 L/acre.

In one embodiment, specific nutrients are added to and/or applied concurrently with the microbe-based product to enhance microbial inoculation and growth. These can include, for example, soluble potash (K2O), magnesium, sulfur, boron, iron, manganese, and/or zinc. The nutrients can be derived from, for example, potassium hydroxide, magnesium sulfate, boric acid, ferrous sulfate, manganese sulfate, and/or zinc sulfate.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C.

Local Production of Microbe-Based Products

In certain embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The microbe growth facilities of the subject invention can be located at the location where the microbe-based product will be used (e.g., a citrus grove). For example, the microbe growth facility may be less than 300, 250, 200, 150, 100, 75, 50, 25, 15, 10, 5, 3, or 1 mile from the location of use.

Because the microbe-based product can be generated locally, without resort to the microorganism stabilization, preservation, storage and transportation processes of conventional microbial production, a much higher density of microorganisms can be generated, thereby requiring a smaller volume of the microbe-based product for use in the on-site application or which allows much higher density microbial applications where necessary to achieve the desired efficacy. This allows for a scaled-down bioreactor (e.g., smaller fermentation vessel, smaller supplies of starter material, nutrients and pH control agents), which makes the system efficient and can eliminate the need to stabilize cells or separate them from their culture medium. Local generation of the microbe-based product also facilitates the inclusion of the growth medium in the product. The medium can contain agents produced during the fermentation that are particularly well-suited for local use.

Locally-produced high density, robust cultures of microbes are more effective in the field than those that have remained in the supply chain for some time. The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

The microbe growth facilities of the subject invention produce fresh, microbe-based compositions, comprising the microbes themselves, microbial metabolites, and/or other components of the medium in which the microbes are grown. If desired, the compositions can have a high density of vegetative cells or propagules, or a mixture of vegetative cells and propagules.

In one embodiment, the microbe growth facility is located on, or near, a site where the microbe-based products will be used (e.g., a citrus grove), for example, within 300 miles, 200 miles, or even within 100 miles. Advantageously, this allows for the compositions to be tailored for use at a specified location. The formula and potency of microbe-based compositions can be customized for specific local conditions at the time of application, such as, for example, which soil type, plant and/or crop is being treated; what season, climate and/or time of year it is when a composition is being applied; and what mode and/or rate of application is being utilized.

Advantageously, distributed microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell-count product and the associated medium and metabolites in which the cells are originally grown.

Furthermore, by producing a composition locally, the formulation and potency can be adjusted in real time to a specific location and the conditions present at the time of application. This provides advantages over compositions that are pre-made in a central location and have, for example, set ratios and formulations that may not be optimal for a given location.

The microbe growth facilities provide manufacturing versatility by their ability to tailor the microbe-based products to improve synergies with destination geographies. Advantageously, in preferred embodiments, the systems of the subject invention harness the power of naturally-occurring local microorganisms and their metabolic by-products to improve GHG management.

The cultivation time for the individual vessels may be, for example, from 1 to 7 days or longer. The cultivation product can be harvested in any of a number of different ways.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Compositions

Exemplified herein is a composition according to certain embodiments of subject invention for use in reducing GHGs, improving carbon utilization, and/or enhancing sequestration of carbon. This example is not to be intended as limiting. Formulations comprising other species of microorganisms, either in lieu of, or in addition to, those exemplified here, may be included in the composition.

The composition comprises a microbial inoculant comprising a *Trichoderma* spp. fungus and a *Bacillus* spp. bacterium. In specific instances, the composition comprises *Trichoderma harzianum* and *Bacillus amyloliquefaciens*. Even more specifically, the strain of *B. amyloliquefaciens* can be *B. amyloliquefaciens* NRRL B-67928.

In one embodiment, the composition can comprise from 1 to 99% *Trichoderma* by weight and from 99 to 1% *Bacillus* by weight. In some embodiments, the cell count ratio of *Trichoderma* to *Bacillus* is about 1:9 to about 9:1, about 1:8 to about 8:1, about 1:7 to about 7:1, about 1:6 to about 6:1, about 1:5 to about 5:1 or about 1:4 to about 4:1.

The composition can comprise about $1\times10^6$ to $1\times10^{12}$, $1\times10^7$ to $1\times10^{11}$, $1\times10^8$ to $1\times10^{10}$, or $1\times10^9$ CFU/ml of the *Trichoderma*; and about $1\times10^6$ to $1\times10^{12}$, $1\times10^7$ to $1\times10^{11}$, $1\times10^8$ to $1\times10^{10}$, or $1\times10^9$ CFU/ml of the *Bacillus*.

The composition can be mixed with and/or applied concurrently with additional "starter" materials to promote initial growth of the microorganisms in the composition. These can include, for example, prebiotics and/or nano-fertilizers (e.g., Aqua-Yield, NanoGro™)

One exemplary formulation of such growth-promoting "starter" materials comprises:
Soluble potash (K2O) (1.0% to 2.5%, or about 2.0%)
Magnesium (Mg) (0.25% to 0.75%, or about 0.5%)
Sulfur (S) (2.5% to 3.0%, or about 2.7%)
Boron (B) (0.01% to 0.05%, or about 0.02%)
Iron (Fe) (0.25% to 0.75%, or about 0.5%)
Manganese (Mn) (0.25% to 0.75%, or about 0.5%)
Zinc (Zn) (0.25% to 0.75%, or about 0.5%)
Humic acid (8% to 12%, or about 10%)
Kelp extract (5% to 10%, or about 6%)
Water (70% to 85%, or about 77% to 80%)

The microbial inoculant, and/or optional growth-promoting "starter" materials, are mixed with water in an irrigation system tank and applied to soil.

In specific instances, the composition comprises 10.0% by weight of the microbial inoculant, and 90% by weight water, where the inoculant comprises $1\times10^8$ CFU/mL *Trichoderma harzianum* and $1\times10^9$ CFU/mL of *Bacillus amyloliquefaciens*.

REFERENCES

Brummell, M. E., and S. D. Siciliano. (2011). "Measurement of Carbon Dioxide, Methane, Nitrous Oxide, and Water Potential in Soil Ecosystems." *Methods in Enzymology*. 496:115-137. Doi: 10.1016/B978-0-12-386489-5.00005-1. ("Brummell and Siciliano 2011").

Gougoulias, C., Clark, J. M., & Shaw, L. J. (2014). The role of soil microbes in the global carbon cycle: tracking the below-ground microbial processing of plant-derived carbon for manipulating carbon dynamics in agricultural systems. *Journal of the Science of Food and Agriculture,* 94(12), 2362-2371. https://doi.org/10.1002/jsfa.6577

Government of Western Australia. (2018). "Carbon farming: reducing methane emissions from cattle using feed additives." https://www.agric.wa.gov.au/climate-change/carbon-farming-reducing-methane-emissions-cattle-using-feed-additives. ("Carbon Farming 2018").

Graça J. (2015). Suberin: the biopolyester at the frontier of plants. *Frontiers in chemistry,* 3, 62. https://doi.org/10.3389/fchem.2015.00062. ("Graca 2015").

Kumar, R., Pandey, S., & Pandey, A. (2006). Plant roots and carbon sequestration. Current Science, 91(7), 885-890. Retrieved from https://www.researchgate.net/profile/Rajeew_Kumar/publication/255642030_Plant-_Roots_and_Carbon_Sequestration/links/547ec84c0cf2c1e3d2dc29f0/Plant-Rootsand-Carbon-Sequestration.pdf Lange, M., Eisenhauer, N., Sierra, C., & Bessler, H. (2015). Plant diversity increases soil microbial activity and soil carbon storage. Nature Communications, 6(6707), 1-8. Retrieved from https://www.nature.com/articles/ncomms7707

Malik, A., Blagodatskaya, E., & Gleixner, G. (2013). Soil microbial carbon turnover decreases with increasing molecular size. Soil Biology & Biochemistry, 62, 115-118. Retrieved from https://www.sciencedirect.com/science/article/pii/S0038071713000849

Pidwirny, M. (2006). "The Carbon Cycle". *Fundamentals of Physical Geography,* 2nd Edition. Date Viewed. http://www.physicalgeography.net/fundamentals/9r.html. ("Pidwirny 2006").

Six, J., Frey, S., Thiet, R., & Batten, K. (2006). Bacterial and fungal contributions to carbon sequestration in agroecosystems. Soil Science Society of America, 70, 555-569.

Sparks, D. L., Page, A. L., Helmke, P. A., Loeppert, R. H., Soltanpou, P. N., Tabatabai, M. A., Johnston, C. T., Sumner, M. E. (1996). Methods of Soil Analysis. Part 3: Chemical Methods. Number 5 in the Soil Science Society of America Book Series. Madison, WI.

United States Environmental Protection Agency. (2016). "Climate Change Indicators in the United States." https://www.epa.gov/sites/production/files/2016-08/documents/climate_indicators_2016.pdf. ("EPA Report 2016").

United States Environmental Protection Agency. (2016). "Overview of Greenhouse Gases." *Greenhouse Gas Emissions.* https://www.epa.gov/ghgemissions/overview-greenhouse-gases. ("Greenhouse Gas Emissions 2016").

Xu, X., Thornton, P. E., & Post, W. M. (2013). A global analysis of soil microbial biomass carbon, nitrogen and phosphorus in terrestrial ecosystems. Global Ecology and Biogeography, 22(6), 737-749. https://doi.org/10.1111/geb.12029

Zhou, J., Xue, K., Xie, J., Deng, Y., Wu, L., & Cheng, X. (2012). Microbial mediation of carbon-cycle feedbacks to climate warming. Nature Climate Change, 2, 106-110. Retrieved from https://www.nature.com/articles/doi:10.1038%2Fnclimate1331

We claim:

1. A method of sequestering carbon in plant and/or soil matter, which comprises applying a composition comprising one or more beneficial microorganisms to a plant and/or to soil in which a plant is grown such that the one or more microorganisms colonize the soil and/or roots of the plant, wherein the beneficial microorganisms are selected from bacteria, yeasts and/or fungi,
wherein colonization by the microorganisms provides one or more benefits to the plant that result in enhanced utilization and storage of carbon via enhanced growth and/or health of aerial and/or subterranean tissue of the plant,
wherein the enhanced growth and/or health of the aerial and/or subterranean plant tissue results in enhanced accumulation of one or more degradation-resistant organic polymers in the plant tissue, said degradation-resistant organic polymers being selected from suberin, cutin, cutan and lignin;
wherein the plant is an annual plant or a crop plant, and wherein portions of the aerial and/or subterranean plant tissue are left behind after the plant's death and/or after harvesting of the plant; and
wherein the portions of the aerial and/or subterranean plant tissue that are left behind are covered by soil at a depth that is not disturbed by tilling, and wherein the degradation-resistant organic polymer does not decompose in the soil for at least 1 year after the death and/or harvest of the plant; and wherein the at least one of the beneficial microorganisms is selected from *Trichoderma harzianum, Trichoderma viride, Trichoderma koningii, Trichoderma guizhouse, Bacillus amyloliquefaciens, Bacillus subtilis, Bacillus megaterium, Bacillus polymyxa, Bacillus licheniformis, Brevibacillus laterosporus, Meyerozyma guilliermondii, Pichia occidentalis, Wickerhamomyces anomalus,* and *Debaryomyces hansenii.*

2. The method of claim 1, wherein the composition is applied directly to the plant's roots.

3. The method of claim 1, wherein the composition is applied to the soil.

4. The method of claim 1, wherein the composition is applied to the plant and/or to the soil using an irrigation system.

5. The method of claim 1, wherein the composition is applied alongside a source of one or more nutrients selected from nitrogen, phosphorous, and potassium.

6. The method of claim 1, wherein the composition is applied to the plant and/or soil contemporaneously with prebiotics selected from kelp extract, fulvic acid, chitin, humate and humic acid.

7. The method of claim 1, wherein the composition is sprayed onto the plant and/or a surrounding environment of the plant using a handheld sprayer.

8. The method of claim 1, further comprising performing a measurement to assess an effect of the method on sequestering carbon.

9. The method of claim 8, wherein the measurement comprises performing an analysis of plant tissue to quantify the accumulation of the degradation-resistant organic polymers in the plant tissue.

10. The method of claim 8, wherein the measurement comprises extracting the degradation-resistant organic polymers from the soil and/or the plant tissue and performing LC, GC, NMR spectroscopy, Raman spectroscopy, mass spectrometry, or FTIR spectroscopy on an extracted degradation-resistant organic polymer to quantify the accumulation of the polymer in the soil and/or plant tissue.

11. The method according to claim 1, wherein the beneficial microorganism is *B. amy* NRRL B-67928.

12. A method of sequestering carbon in plant and/or soil matter, which comprises applying a composition comprising one or more beneficial microorganisms to a plant and/or to soil such that the one or more microorganisms colonize the plant's roots and/or the soil, wherein the beneficial microorganisms are selected from bacteria, yeasts and/or fungi, wherein the colonization by the microorganisms provides one or more benefits to the plant that result in enhanced utilization and storage of carbon via enhanced growth and/or health of the plant's aerial and/or subterranean plant tissue, wherein the enhanced growth and/or health of the aerial and/or subterranean plant tissue results in enhanced accumulation of at least one degradation-resistant organic polymers in the plant tissue, said degradation-resistant organic polymers being selected from suberin, cutin, cutan and lignin; wherein the method further comprises performing a measurement to assess the effect of the method on sequestering carbon; wherein at least one of the beneficial microorganisms is selected from *Trichoderma harzianum, Trichoderma viride, Trichoderma koningii, Trichoderma guizhouse, Bacillus amyloliquefaciens, Bacillus subtilis, Bacillus megaterium, Bacillus polymyxa, Bacillus licheniformis, Brevibacillus laterosporus, Meyerozyma guilliermondii, Pichia occidentalis, Wickerhamomyces anomalus,* and *Debaryomyces hansenii*; wherein portions of the aerial and/or subterranean plant tissue are left behind after the plant's death and/or after harvesting of the plant; and wherein the portions of the aerial and/or subterranean plant tissue that are left behind are covered by soil at a depth that is not disturbed by tilling, and wherein the degradation-resistant organic polymer does not decompose in the soil for at least 1 year after the death and/or harvest of the plant and wherein the measurement comprises extracting the degradation-resistant organic polymer from the soil and/or the plant tissue and performing LC, GC, NMR spectroscopy, Raman spectroscopy, mass spectrometry, or FTIR spectroscopy on the extracted degradation-resistant organic polymer to quantify the accumulation of the polymer in the soil and/or plant tissue.

13. The method of claim 12, wherein the composition is applied directly to the plant's roots.

14. The method of claim 12, wherein the composition is applied to the soil.

15. The method of claim 12, wherein the composition is applied to the plant and/or to the soil using an irrigation system.

16. The method of claim 12, wherein the composition is applied alongside a source of one or more nutrients selected from nitrogen, phosphorous, and potassium.

17. The method of claim 12, wherein the composition is applied to the plant and/or soil contemporaneously with prebiotics selected from kelp extract, fulvic acid, chitin, humate and humic acid.

18. The method of claim 12, wherein the composition is sprayed onto the plant and/or a surrounding environment of the plant using a handheld sprayer.

* * * * *